US00PP16664P2

(12) United States Plant Patent
Zary

(10) Patent No.: US PP16,664 P2
(45) Date of Patent: Jun. 20, 2006

(54) FLORIBUNDA ROSE PLANT NAMED 'JACZEEZE'

(50) Latin Name: *Rosa hybrida*
Varietal Denomination: JACzeeze

(75) Inventor: Keith W. Zary, Agoura Hills, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 103 days.

(21) Appl. No.: 10/969,690

(22) Filed: Oct. 19, 2004

(51) Int. Cl.
*A01H 5/00* (2006.01)

(52) U.S. Cl. ..... Plt./144

(58) Field of Classification Search ..... Plt./144, Plt./145, 133, 134
See application file for complete search history.

*Primary Examiner*—Howard J. Locker
(74) *Attorney, Agent, or Firm*—Klarquist Sparkman LLP

(57) ABSTRACT

Floribunda rose plant having long stems; large clusters of flowers; strong fragrance; healthy, dark green, glossy foliage and ease of root production from softwood cuttings.

1 Drawing Sheet

Genus and species: *Rosa hybrida.*
Variety denomination: 'JACzeeze'.

ORIGIN OF THE INVENTION

The present invention relates to a new and distinct variety of floribunda rose plant named 'JACzeeze' which was originated by me by crossing an unnamed, unpatented seedling (Sexy Rexy×unnamed red seedling), with the variety 'Vie en Rose' (not patented).

BACKGROUND OF THE INVENTION

The primary objective of this breeding was to produce a new rose variety having the root vigor, healthy foliage and rapid bloom of the pink female floribunda parent combined with the large cluster size, fragrance and long cutting stems of the pink with white reverse flowers of the male floribunda parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Long stems.
2. Large flower clusters.
3. Strong fragrance.
4. Healthy, dark green, glossy foliage.
5. Ease of root production from softwood cuttings.

Asexual reproduction of this new variety by cuttings, as performed at Wasco, Calif., shows that the foregoing and all other characteristics and distinctions come true to form and are established and transmitted through succeeding propagations.

Comparison with Parents

'JACzeeze' differs from both parents in its white flower color, the female parent having pink flowers, the male parent having pink with white reverse flowers.

Comparison with Similar Variety

A similar variety is 'Iceberg' although 'JACzeeze' has larger clusters, smaller flowers, is much more upright and has much more fragrance.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—Unnamed seedling, (not patented) (Sexy Rexy×unnamed red seedling).

*Pollen parent.*—'Vie en Rose' (unpatented) (Charleston×Friesia).

FLOWER

Observations made of plants commencing at four years of age in a garden environment at Somis, Calif., from January 2003 to August 2004.

Blooming habit: Continuous.

Bud:

*Size.*—About 25 mm long and 17 mm in diameter when the petals start to unfurl.

*Form.*—The bud form is long, pointed ovoid.

*Color.*—When sepals first divide, bud color is Yellow-White Group 158B with areas of Greyed-Purple Group 183D, especially on petal edges. When half blown, the upper sides of the petals are White Group 155B and the lower sides of the petals are White Group 155B.

*Sepals*.—Color: Upper surface: Yellow-Green Group 146D with Yellow-Green Group 144D at base. Lower surface: Yellow-Green Group 144A with prominent Yellow-Green Group 144C vein in center of sepal from base to apex. Length: 22–26 mm. Width: 7–9 mm. Shape: Subulate. Surface texture: Upper: Hoary; Lower: Glandular. There are three normally appendaged sepals. There are two unappendaged sepals with hairy edges.

*Receptacle*.—Color: Yellow-Green Group 144A. Shape: Funnel. Size: Small, about 5 mm long×5–6 mm wide. Surface: Hairy.

*Peduncle*.—Length: Short, averaging about 40–60 mm. Surface: Glandular. Color: Young: Greyed-Purple Group 184A. Mature: Yellow-Green Group 144A. Strength: Stiff.

Bloom:

*Size*.—Medium. Average open diameter is about 8–9 cm.

*Borne*.—Several together in pyramidal clusters of 3–7 blooms.

*Stems*.—Strength: Strong. Average length is about 45 cm with a diameter of 4–7 mm.

*Form*.—When first open: High centered. Permanence: Flattens.

*Petalage*.—Number of petals under normal conditions: 20.

*Color*.—The upper sides of the petals are White Group 155B. The reverse sides of the petals are White Group 155B. The base of each petal has a small 2 mm×2 mm Yellow Group 3D color spot. The major color on the upper side is White Group 155B.

*Variegations*.—None observed.

*Discoloration*.—The general tonality at the end of the first day: No change. At the end of the third day: No change.

*Fragrance*.—Strong, honeysuckle.

Petals:

*Texture*.—Thick.

*Shape*.—Smooth.

*Surface*.—Round.

*Margin*.—Smooth and entire. Apex Shape: Rounded. Base Shape: Rounded.

*Form*.—Tips slightly recurved.

*Arrangement*.—Imbricated.

*Petaloids*.—Number: 2–5. Size: Length — 15–25 mm. Width — 5–15 mm. Color: White Group 155 B.

*Persistence*.—Petals drop off cleanly before drying.

*Lastingness*.—On the plant: Fair (about 4–5 days). As a cut flower: Fair (about 5–6 days).

Reproductive parts:

*Stamens*.—Number: 100–200. Length: 8–12 mm. Anthers: Length: 2 mm. Color: Yellow-Orange Group 16C. Arrangement: Regular around styles. Filaments: Color: Yellow Group 4C. Length: 6–10 mm. Pollen: Color: Yellow-Orange Group 16A.

*Pistils*.—Number: 60–80. Length: 5–8 mm. Styles: Color: Yellow-Green Group 145D. Length: 4–7 mm. Stigmas. Color: Yellow-White Group 158A. Length: 1 mm.

*Hips*.—None observed.

PLANT

*Form*.—Bush.

*Growth*.—Very vigorous, upright, branching.

*Age at maturity*.—Two years.

*Mature plants*.—Height: 120 cm. Width: 80 cm.

*Rootstock*.—Own root.

Foliage: Number of leaflets on normal mid-stem leaves: 5 or 7.

*Size*.—Large. About 13–14 cm long×11–12 cm wide.

*Quantity*.—Abundant.

*Color*.—New foliage: Upper side: Greyed-Red Group 182A. Lower side: Greyed-Red Group 182A. Old foliage: Upper side: Green Group 139A. Lower side: Green Group 137C.

Leaflets:

*Size*.—About 60 mm long×30 mm wide.

*Shape*.—Ovate.

*Base shape*.—Oblique.

*Apex shape*.—Acuminate.

*Texture*.—Leathery.

*Edge*.—Serrated.

*Serrations*.—Single.

*Petiole*.—Color: Yellow-Green Group 146C.

*Petiole rachis*.—Color: Yellow-Green Group 146B. Underside: Rough with prickles and glands.

*Stipules*.—Length: 15 mm. Smooth but edged in glands.

*Disease resistance*.—Resistant to mildew and rust and susceptible to blackspot under normal growing conditions.

*Pest resistance*.—Not observed.

*Vein color*.—Green Group 137D.

*Venation pattern*.—Reticulate.

Wood:

*New wood*.—Color: Greyed-Red Group 181B. Bark: Smooth.

*Old wood*.—Color: Yellow-Green Group 144A. Bark: Smooth.

Prickles:

*Quantity*.—On main canes from base: Ordinary, 10 prickles per 15 cm. On laterals from main canes: Few, 4 prickles per 15 cm.

*Form*.—Hooked downward.

*Length*.—8–10 mm.

*Color when young*.—Greyed-Red Group 181B.

*Color when mature*.—Greyed-Yellow Group 160C.

Small prickles:

*Quantity*.—On main stalks: None. On laterals: None.

Winter hardiness: Hardy to Zone 5.

I claim:

1. A new and distinct variety of rose plant of the floribunda class, substantially as herein shown and described, characterized particularly by long stems; large flower clusters; strong fragrance; healthy, dark green, glossy foliage and ease of root production from softwood cuttings.

* * * * *

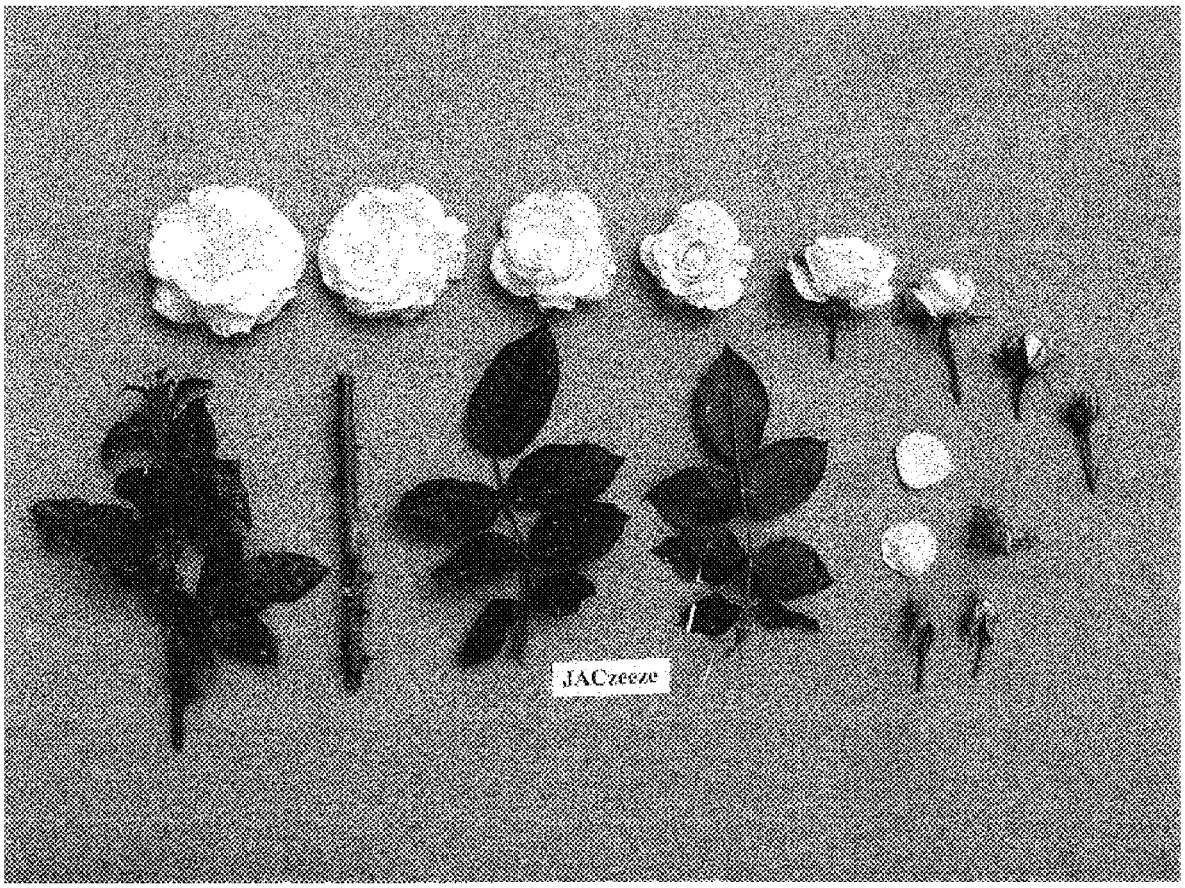
JACzeeze